(12) United States Patent
Bennett et al.

(10) Patent No.: US 7,150,740 B2
(45) Date of Patent: *Dec. 19, 2006

(54) URINARY CATHETER SYSTEM

(75) Inventors: Rita Latterman Bennett, San Clemente, CA (US); Thomas F. Fangrow, Jr., Mission Viejo, CA (US); Evelyn L. Foss, Santa Margarita, CA (US)

(73) Assignee: ICU Medical, Inc., San Clemente, CA (US)

( * ) Notice: Subject to any disclaimer, the term of this patent is extended or adjusted under 35 U.S.C. 154(b) by 9 days.

This patent is subject to a terminal disclaimer.

(21) Appl. No.: 10/945,757

(22) Filed: Sep. 21, 2004

(65) Prior Publication Data

US 2005/0038414 A1    Feb. 17, 2005

Related U.S. Application Data

(63) Continuation of application No. 09/511,555, filed on Feb. 23, 2000, now Pat. No. 6,793,651.

(51) Int. Cl.
*A61M 27/00* (2006.01)

(52) U.S. Cl. ........................ 604/544; 604/327

(58) Field of Classification Search ............... 604/544, 604/327–331, 264, 523, 257, 262, 533–535, 604/537–541, 543, 256, 904; 251/149.1
See application file for complete search history.

(56) References Cited

U.S. PATENT DOCUMENTS

| | | |
|---|---|---|
| 5,113,911 A | 5/1992 | Hirsh |
| 5,230,706 A | 7/1993 | Duquette |
| 5,429,620 A | 7/1995 | Davis |
| 5,509,912 A | 4/1996 | Vaillancourt et al. |
| 5,616,138 A | 4/1997 | Propp |
| 5,674,206 A | 10/1997 | Alton et al. |
| 5,685,866 A | 11/1997 | Lopez |
| 5,690,612 A | 11/1997 | Lopez et al. |
| 5,694,686 A | 12/1997 | Lopez |
| 5,695,466 A | 12/1997 | Lopez et al. |
| 5,727,594 A | 3/1998 | Choksi |
| 5,848,994 A | 12/1998 | Richmond |
| 5,873,862 A | 2/1999 | Lopez |
| 5,901,942 A | 5/1999 | Lopez |
| 5,919,146 A | 7/1999 | Propp |
| 5,928,204 A | 7/1999 | Lopez |
| 5,971,965 A | 10/1999 | Mayer |
| 5,984,902 A | 11/1999 | Moorehead |
| 6,007,521 A | 12/1999 | Bidwell et al. |

(Continued)

OTHER PUBLICATIONS

Closed Drainage Bag, Cat. No. 5912, Baxter, Oct. 1993.

(Continued)

*Primary Examiner*—Michele Kidwell
(74) *Attorney, Agent, or Firm*—Knobbe Martens Olson & Bear LLP

(57) ABSTRACT

The urinary catheter system includes a urinary catheter, a connector and a medical implement which is readily attached to or removed from the connector. When a medical implement such as a collection appliance is attached to the connector, fluid such as urine can flow from the patent and into the collection appliance. Alternatively, when a syringe is attached to the connector, the catheter system may be irrigated to remove debris and other foreign matter, or the syringe may be used to provide medication to the patient. The system is preferably a closed system in which the connector includes a resealable valve which prevents the flow of fluid through the connector if a medical implement is not attached.

5 Claims, 2 Drawing Sheets

U.S. PATENT DOCUMENTS

| | | |
|---|---|---|
| 6,029,076 A | 2/2000 | Fiddian-Greene et al. |
| 6,039,302 A | 3/2000 | Cote, Sr. et al. |
| 6,102,888 A | 8/2000 | Walker |
| 6,168,137 B1 | 1/2001 | Paradis |
| 6,217,560 B1 | 4/2001 | Ritger et al. |
| 6,240,960 B1 | 6/2001 | Fillmore |
| 6,261,282 B1 | 7/2001 | Jepson et al. |
| 6,270,053 B1 | 8/2001 | Eshel |
| 6,344,033 B1 | 2/2002 | Jepson et al. |

OTHER PUBLICATIONS

Urine Sampling Unit, Cat. No. 9680, Baxter, Feb. 1992.

URINARY CATHETER SYSTEM

RELATED APPLICATIONS

This application is a continuation of U.S. application Ser. No. 09/511,555, filed Feb. 23, 2000, now U.S. Pat. No. 6,793,651, the entirety of which is hereby incorporated by reference herein.

BACKGROUND OF THE INVENTION

1. Field of the Invention

The present invention generally relates to catheters and, in particular, to urinary catheters. More particularly, the present invention relates to a urinary catheter system with a urinary catheter connector.

2. Description of the Related Art

The manipulation and movement of fluids is very important in various hospital and medical settings. The movement of fluids frequently requires various connectors and adapters for facilitating the movement of fluids between different points. For example, urinary drainage systems are known to provide a pathway for urine to flow from the body of a patient into a urine receptacle. These drainage systems frequently use indwelling urinary catheters or drainage tubes which are connected to a drainage device hub which, in turn, is connected to the urine receptacle. This system therefore provides a flow path for the urine from the patient to the urine receptacle.

Known urinary drainage systems typically connect one end of the indwelling urinary catheter to the drainage hub by a clamp or other known type of connector. The drainage hub is connected to the urine receptacle by a male type connector such as a male Luer Lock. As known, the urine receptacle may include a "bedside" collection bag, a leg collection bag or stoma bag.

In all instances of conventional urinary drainage systems, detachment of the urine receptacle from the drainage system requires the disconnection of the receptacle from the drainage hub, thus creating an opening in the system. This open drainage system provides a pathway through which bacteria and other infectious matter can travel through the drainage system and into the urinary system of the patient, which may result in severe urinary tract problems such as urinary tract infections. Thus, each time the urine receptacle is removed from a conventional urinary system, for example for replacement or cleaning, this increases the risk of infection for the patient.

Additionally, known urinary drainage systems frequently require irrigation of the indwelling urinary catheter to provide medication to the bladder or other parts of the patient's urinary system. Irrigation of the indwelling urinary catheter may also be required to remove debris such as blood clots from the catheter. The irrigation of the indwelling catheter, whether to provide medication or remove debris, also requires disconnection of the urine receptacle and opening of the system to allow a syringe or other medical instrument to be attached to the drainage hub. The syringe or medical instrument is then used to irrigate or provide medication to the patient, and then it is disconnected from the drainage hub and a urine receptacle is reattached. This repeated opening of the drainage system greatly increases the risk that bacteria and other infectious materials will travel into the urinary system of the patient and cause a urinary tract infection.

Additionally, known urinary drainage systems require that the urine receptacle be removed so that urine samples can be obtained and other testing or treatment may be performed. Thus, each time testing or treatment of the patient is required, which may be frequent, the system must be opened and this further exposes the patient to the risk of infection and other maladies.

Further, it is known that the urine receptacle is often a source for bacteria and other infectious materials because it may act as an incubator in which various organisms grow. Accordingly, in order to decrease the possibility of an infection, patients using known urinary drainage systems and health care providers are cautioned never to have the collection bag at a height greater than the bladder of the patient because that may allow urine from the collection bag to flow into the urinary catheter or urinary system of the patient. Additionally, all patients and health care providers are informed never to move or shift the collection bag so that urine flows into the urinary catheter or urinary system of the patient. Finally, patients and health care providers must use extreme caution during the connection, disconnection and opening of the drainage system because of the risk that material from the urine receptacle will enter the urinary catheter or urinary system of the patient.

Moreover, current urinary drainage systems having an open hub permit the leakage of urine during disconnection of the urine receptacle. Contact with this body fluid by the health care provider may result in associated pathogen-caused diseases as is well known in the art. Thus, it is desirable to prevent contact of the body fluid and health care workers or patients. The present invention, as described below, advantageously eliminates the potential contact of a patient's bodily fluids and the health care provider and patient's skin.

SUMMARY OF THE INVENTION

A need therefore exists for a urinary catheter system which eliminates the above-described disadvantages and problems.

One aspect of the present invention is a urinary catheter system which includes a urinary catheter and a connector including a proximal end and a distal end. In particular, the system desirably includes an indwelling urinary catheter which is attached to the proximal end of the connector and the connector includes a bi-directional, resealable valve that allows fluid to flow in either direction when open. The system preferably includes a medical implement which is removably attached to the connector. The medical implement may include a collection appliance with a reservoir that may be filled with fluid. The collection appliance preferably includes a one-way valve so that once fluid enters the appliance, it cannot flow back through the system. This decreases the risk of infection to the patient and health care provider because the fluid is trapped in the appliance. Additionally, because the valve inside the connector is resealable, the collection appliance or other medical implement may be removed and fluid will not flow through the valve. Accordingly, the collection appliance or medical implement can be readily replaced, cleaned or removed to allow sampling, testing or treatment of the patient to occur without leaking or spilling of the fluid contained in the system.

Another aspect of the present invention is a urinary catheter system which facilitates fluid flow between the patient and the collection appliance while maintaining a sterile environment. Advantageously, because the connector can be easily swabbed with a suitable substance such as alcohol or disinfectant, the connector can be sterilized and reused. Thus, various medical implements can be connected and disconnected to the system and a sterile environment remains. Additionally, because the resealable valve closes the fluid pathway through the connector if a suitable medical implement is not attached to the connector, bacteria and other foreign matter cannot enter the urinary catheter or urinary system of the patient. Consequently, this closed system greatly reduces the risk of infection to the patient.

Yet another aspect of the invention is that the connector includes a proximal end which is adapted to be in fluid connection with a urinary catheter. In particular, the proximal end of the connector includes an elongated body with one or more outwardly extending annular flanges. The elongated body is sized and configured to be inserted into an end of the urinary catheter and the flanges are sized and configured for secure, fluid-tight connection of the catheter and connector. The annular flanges preferably have an angled first surface and an angled second surface to create a secure friction or interference fit between the catheter and the proximal end of the catheter.

Yet another aspect of the invention is that the connector includes a distal end which has an adaptor that enables the connector to be removably attached to medical implements such as a syringe or collection appliance. Preferably, the adaptor is a Luer Lock-type connector that provides a secure, fluid-tight connection that can be easily released. The threaded luer-type connector advantageously allows various medical implements and instruments such as syringes or any of a wide variety of conduits and connectors used in medical applications to be connected to the urinary catheter system.

The present invention also includes a method of transferring fluid from a patient to a remote source. Alternatively, fluid from a remote source can be transferred to the patient. This is possible because the connector provides two-way fluid communication. Thus, in one embodiment, the urinary catheter system allows fluid from the urinary system of the patient to flow through the urinary catheter and, if a collection appliance is attached, the fluid flows into the collection appliance. On the other hand, if the collection appliance is not attached to the system, the system is closed and no fluid or other materials can pass through the system. In another embodiment, a medical implement such as a syringe may be attached to the system and the syringe, for example, may provide irrigation or medication.

Advantageously, the urinary catheter connector of the present invention substantially reduces the risk of urinary tract infection because it is a closed system which does not permit fluids, bacteria or other materials to travel through the urinary catheter and into the urinary system of the patient. Significantly, because the urinary catheter connector substantially reduces the number of urinary tract infections, this reduces the health care costs associated with the treatment of urinary infections and significantly improves the quality of life of the patient. Additionally, it may improve the quality of life for urinary catheter users because it greatly simplifies the connection and removal of the collection appliances and other medical implements. Importantly, the urinary catheter connector also decreases the risk of disease or illness for health care providers because of contact with bodily fluids and their associated pathogen caused diseases.

Further aspects, features and advantages of the present invention will become apparent from the detailed description of the preferred embodiments that follows.

BRIEF DESCRIPTION OF THE DRAWINGS

The appended drawing contains a figure of a preferred embodiment of the present urinary catheter system. The above-mentioned features of the urinary catheter system, as well as other features, will be described in connection with the preferred embodiments. The illustrated embodiment, however, is only intended to illustrate the invention and not limit the invention. The drawings contain the following figures.

DETAILED DESCRIPTION OF THE PREFERRED EMBODIMENT

The present invention involves a urinary catheter system. The principles of the present invention, however, are not limited to urinary catheter systems. It will be understood that, in light of the present disclosure, the urinary catheter system disclosed herein can be successfully used in connection with other types of catheters, catheter systems and medical instruments.

Additionally, to assist in the description of the urinary catheter system, words such as proximal and distal are used to describe the accompanying figures. It will be appreciated, however, that the present invention can be located in a variety of desired configurations and arrangements. Further, the term "medical implement" is used to denote any medical tool or instrument known to those of skill in the art that can be used with the present invention. A detailed description of the urinary catheter system now follows.

Figure 1:
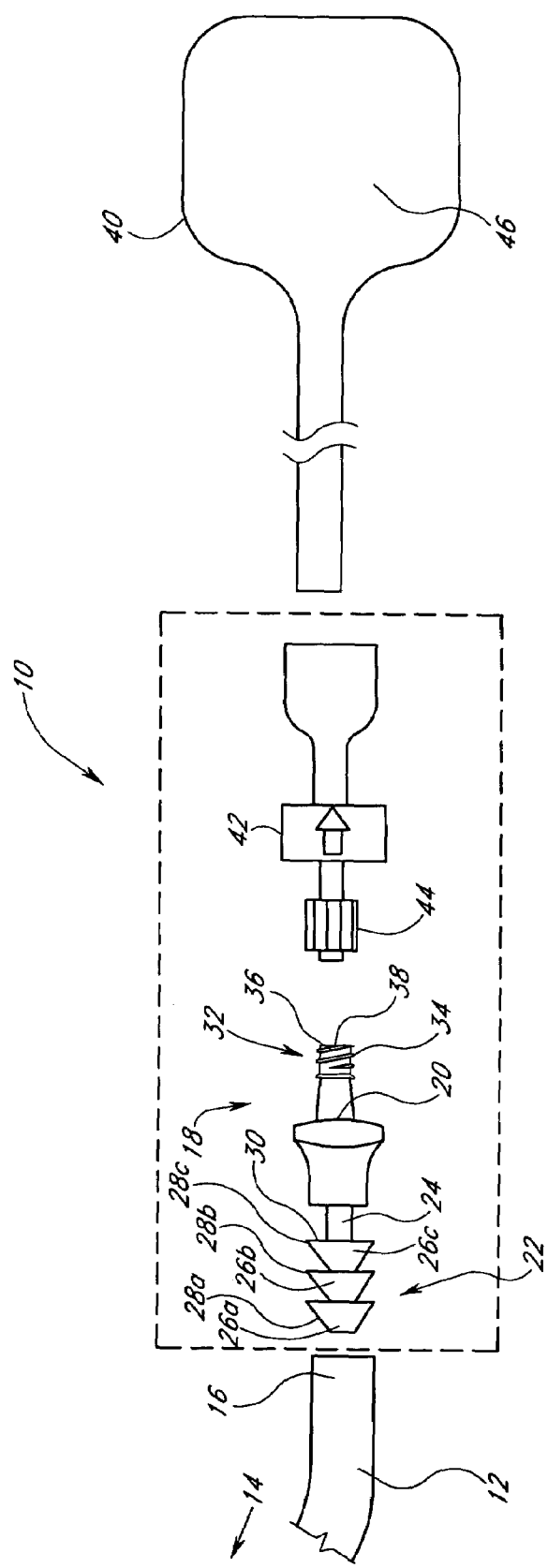
FIG. 1 is an exploded schematic view of the urinary catheter system in accordance with a preferred embodiment of the present invention.

As seen in FIG. 1, the urinary catheter system 10 preferably includes an indwelling urinary catheter 12 which includes a hollow tube which creates a fluid flow pathway. The catheter 12 has a first end 14 which is inserted within a patient (not shown) in any desired manner and a second end 16 which is attached to a connector 18. The connector 18 has a generally tubular body 20 with an internal cavity which allows fluid to flow through the body 20. The connector 18 also preferably includes a valve (not shown) which controls the flow of fluid through the body 20. The valve is preferably a two-way valve that allows fluid to flow in either direction through the valve. More preferably, the valve allows fluid to flow through the connector 18 when a medical implement is attached to the distal end of the connector, as described in detail below, and the valve is closed and sealed when a medical implement is not attached to the distal end of the connector. Most preferably, the connector 18 includes a resealable valve as disclosed in U.S. Pat. No. 5,685,866 issued on Nov. 11, 1997 or U.S. Pat. No. 5,694,686 issued on Dec. 9, 1997, which are assigned to the same assignee as the present application and are hereby incorporated by reference in their entirety. However, any of a number of known connectors providing two way flow of fluid may be used with regard to the present invention. For example, two way connectors sold by Baxter Healthcare Corporation, Abbott Laboratories, McGaw, or Ivac may be used in connection with the disclosed urinary catheter system, as will be easily understood by those of skill in the art. In fact, any two way connector which permits flow of fluid therethrough upon attachment of a medical implement and ceases flow of fluid therethrough upon removal of said medical implement may be used in connection with the disclosed invention. Thus, use of known connectors in this novel implementation is expressly contemplated herein.

The proximal end 22 of the connector 18 is in fluid communication with the urinary catheter 12. As shown in FIG. 1, the second end 16 of the catheter 12 preferably includes an elongated hollow body 24 with one or more annular, outwardly extending flanges. As shown in the accompanying figure, the connector 18 includes three flanges 26a, b and c, but the connector may include any number of flanges, including no flanges. The flanges 26a, b and c include an angled first surface 28a which is preferably at an angle between about 10° and about 60° with respect to a longitudinal axis extending through the connector 18. More preferably, the angled surfaces 28a, b and c are at about a 60° angle, but the angle could be larger or smaller and different flanges may have different angles or sizes. For example, the flanges 26a, b and c near the end of the connector 18 may be slightly smaller or at a smaller angle relative to the longitudinal axis than the flanges near the center of the connector 18. The flanges 26a, b and c also include a second angled surface 30 which is generally perpendicular to the longitudinal axis, but the second surface may be at any suitable angle. These flanges 26a, b and c are sized and configured to allow at least a portion of the elongated hollow body 24 to be inserted into the opening in the end 16 of the urinary catheter 12. The flanges 26a, b and c desirably create a secure, fluid tight, mechanical connection between the connector 18 and the catheter 12 that prevents the connector from being easily removed from the catheter. Alternatively, the proximal end 22 of the connector 18 may be secured to the distal end 16 of the indwelling catheter 12 by any one of a number of means known to those of skill in the art, including bonding, adhesives or other connector means, creating a fluid tight seal between the catheter 12 and connector 18.

Alternatively, the proximal end 22 of the connector 18 may be sized such that the internal diameter of the cavity in the connector 18 at the proximal end 22 thereof is larger than the outside diameter of the end 16 of the catheter 12. In this configuration, the internal surface (not shown) of the proximal end 22 of the connector 18 may be configured with flanges (not shown) so that the second end 16 of the catheter 12 may be inserted within the cavity in the proximal end 22 of the connector 18, but not readily removable therefrom, thus, creating a fluid tight seal as will be understood by those of skill in the art.

The distal end 32 of the connector 18 preferably includes an adaptor 34 that allows the connector 18 to be releasably attached to various medical implements including syringes, conduits, tubing and the like. Preferably, the adaptor 34 comprises threads adapted to be removably secured to a luer lock of a medical implement. Preferably, the connector 18 can be readily connected and disconnected to various medical implements, as will be easily understood by those of skill in the art. As shown in FIG. 1, conventional Luer Lock threads 36 are provided on the outer surface of the distal end 32 of the connector 18. This allows the distal end 32 of the connector 18 to be secured to any compatible device known to those skilled in the art with a Luer Lock-type connection. It is contemplated, however, that the adaptor 34 can be of different sizes and configurations to accommodate the attachment of other connectors and devices thereto.

The distal end 32 of the connector 18 preferably includes a generally flat outer surface 38 which is preferably generally aligned with a generally flat outer surface of the resealable valve located within the connector. This generally flat distal end 32 of the connector 18 can be easily swabbed with alcohol or other disinfectant to provide sterility without leakage of the disinfectant into the connector. This allows the connector 18 to be readily reused with various medical implements and a sterile connection is maintained because the connector can be easily sterilized after a medical implement is disconnected from the connector and/or before a medical implement is attached to the connector. Further, because the valve inside the connector 18 prevents the flow of fluid through the system 10 unless a desired medical implement is attached to the distal end 32 of the connector 18, the system is closed which prevents undesired fluids and bacteria from entering the system. Thus, the connector 18 is reusable and a sterile environment may be maintained.

As shown in FIG. 1, in a preferred embodiment, the medical implement attached to the connector 18 is a collection appliance 40 with a valve 42 and an adaptor 44. The collection appliance 40, valve 42 and adaptor 44 may be a unitary system or one or more separate components that are interconnected. In greater detail, the adaptor 44 is preferably a male Luer Lock-type connector that is sized and configured to be attached to the adaptor 34 of the catheter 18. The connection of the adopters 34 and 44 establishes a fluid-tight connection between the connector 18 and the collection appliance 40 that allows fluid to flow through the system 10. The valve 42, which may be directly attached to the adaptor 44 or, for example, by a conduit, permits fluid to flow in one direction only so that once fluid enters the collection appliance 40 it cannot escape. Thus, once fluid flows through the valve 42, the fluid is contained within the collection appliance 40 and there can be no flow of fluid from the collection appliance 40 into the connector 18, urinary catheter 12 or urinary system of the patient. This significantly reduces the risk of infection for the patient. It will be understood that the collection appliance 40 includes a reservoir or fluid container 46 and the collection appliance may, for example, be a "bedside" collection bag, a leg bag, a stoma bag or other type of known bag. Alternatively, the collection appliance 40 may be a container, syringe or other type of fluid receiving device such as a toilet or drain.

The medical implement attached to the connector 18 may also be a syringe which is configured to be attached to the adaptor 34 at the distal end of the connector 18. The syringe preferably includes a male Luer Lock-type connector which allows it to be easily locked and released to the adaptor 34 of the connector 18. The syringe may be used to provide medication or other fluids to the urinary system of the patient. The syringe may also be used for irrigation of the connector 18 and catheter 12, for example, to remove debris and other foreign matter. It will be understood that syringes of different sizes and configurations may be used with the system 10, and that any suitable medical implement or instrument may also be used with the system.

During use, the urinary catheter system 10 allows fluid to flow from the urinary system of the patient, through the urinary catheter 12, connector 18, adaptor 44, valve 42 and into the collection appliance 40. In greater detail, urine flows into an indwelling urinary catheter 12. The urine then flows through the connector 18, adaptor 44, one-way valve 42 and into the attached collection appliance 40. Significantly, the lockable connection of the collection appliance 40 to the connector 18 creates a secure flow path for the fluid to travel through the system 10. Advantageously, if the collection appliance 40 is disconnected, the connector 18 reseals and prevents the flow of fluid through the connector. Accordingly, if the collection appliance 40 is being changed or replaced, for example, the connector 18 prevents the flow of fluid until the collection appliance is replaced. Thus, the system 10 is closed and greatly reduces the risk of bacteria or other foreign matter entering the urinary catheter 12 or urinary system of the patient.

Significantly, when the collection appliance 40 is removed from the connector 18, the one-way valve 42 prevents fluid from escaping from the fluid reservoir 46. Thus, handling of the appliance 40 reduces the risk of infection for the patient and the health care provider because bodily fluids are not permitted to be removed from the appliance 40.

Additionally, the system 10 can be used to flow fluid through the connector 18 and into the urinary catheter 12 towards the patient. This allows the urinary catheter 12 and connector 18 to be irrigated to remove debris such as blood clots and other foreign matter. For example, a syringe or other medical implement may be connected to the connector 18 and used to irrigate the system 10 as will be understood by those of skill in the art. Additionally, a syringe or other medical implement may be attached to the connector 18 and used to administer medication or other fluids to the patient or to remove a urine sample through the urinary catheter 12. Thus, the catheter 12 and connector 18 allow fluid to flow in either direction depending upon whether fluid is being withdrawn from the patient or medication or other fluids are being injected into the patient.

The urinary catheter 12 and collection appliance 40 are preferably constructed from known materials such as medically inert plastic and the connector 18 is preferably prepared from plastic with a relatively high hardness, but the connector and other parts of the system can be constructed from other medically inert or other suitable materials known in the art. Additionally, the connector 18 can be provided in a sterile and disposable form such that after its use, it is discarded. However, as described above, the connector 18 can be reused multiple times because it is swabbable with disinfectant and various medical implements such as the collection appliance 40 can be readily connected and disconnected.

Figure 2:
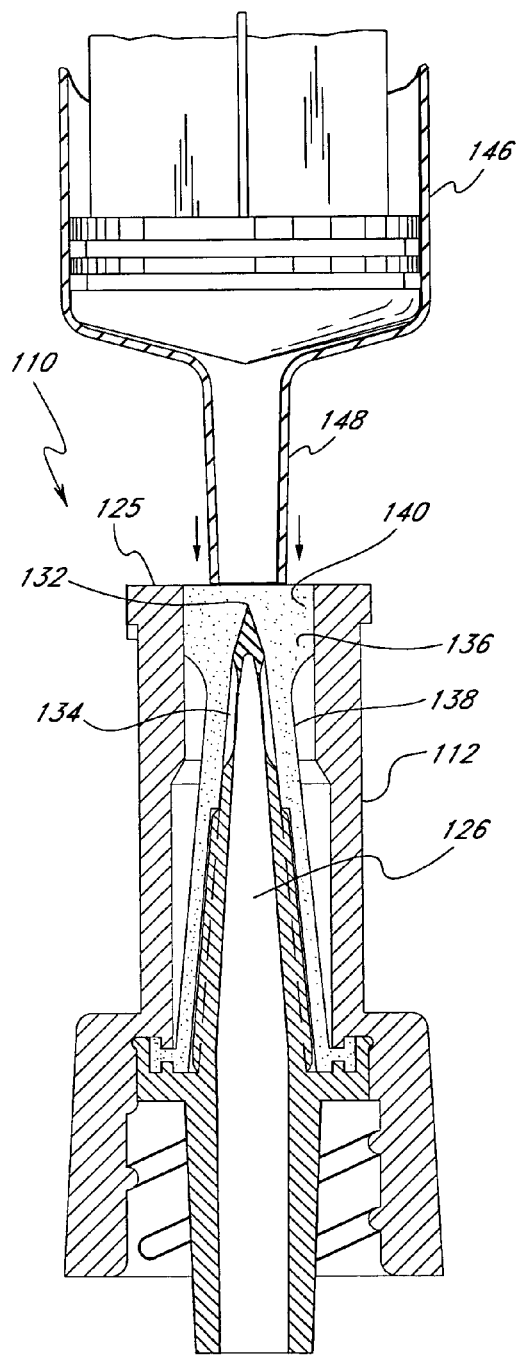
FIG. 2 illustrates a valve in accordance with an embodiment of the invention.
Figure 3:
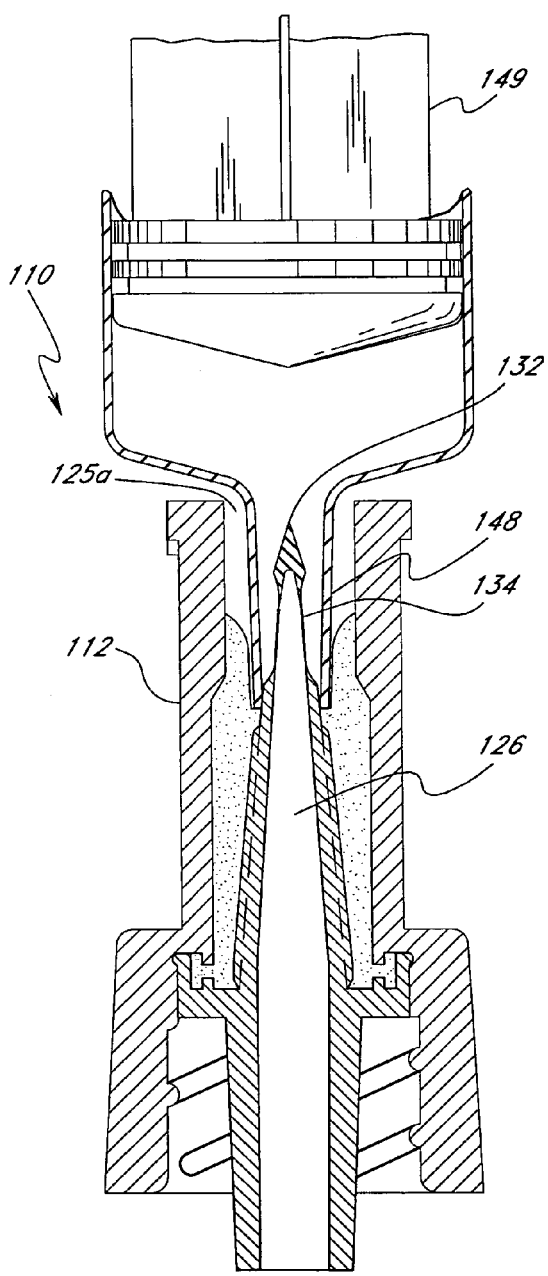
FIG. 3 illustrates a valve in accordance with an embodiment of the invention.

FIGS. 2 and 3 illustrate an embodiment of the invention in which the connector 18 includes a valve 110. In FIG. 2, the medical implement connecting to the proximal end of the valve 110 is a syringe 146. However, this connecting implement could be any number of medical implements known to those of skill in the art. A nose 148 of the syringe 146 is placed on the seal cap 140 inside a lip 125 of the housing 112. The application of pressure on the syringe 146 in the direction of the arrows, as illustrated in FIG. 2 creates pressure on seal cap 140. The resulting downward pressure compresses the seal 136. This pushes the tip 132 of the spike 126 through the seal cap 140 to expose the through-holes 134. Compression is facilitated by the grooves 138. Fluid is now able to flow into the syringe 146, or vice versa, depending on whether fluid is to be withdrawn from the patient or medication injected into the patient. FIG. 3 shows valve 110 opened by insertion of the nose 148 of the syringe 146 into the opening 125a. A syringe plunger 149 in the syringe 146 is retracted thereby creating a vacuum to draw fluid through the valve 110 into the syringe.

Upon removal of the syringe from spike 126, as shown in FIG. 2, the seal 136 is free to return to its original shape and cover through-holes 134. The ability of the seal 136 to return to its original shape is determined by the resiliency of the material used to prepare the seal 136. In addition, the ability of the seal 136 to return to its original shape is facilitated by the protruding ridges 130 formed on the external surface of the spike. During compression, a vacuum may form in the area between the spike 126 and the seal 136, thereby preventing the seal 136 from returning to its original position. The protruding ridges permit air to pass along the spike/seal interface to prevent vacuum formation and allow free return of the seal. The ability of the seal 136 to deform reversibly and return to its original position is particularly useful because (1) it immediately stops fluid flow through the valve 110, (2) it covers the recessed spike 126 to maintain its sterility, and (3) it reduces the risk that the spike could inadvertently pierce another object or person. In addition, since the valve 110 lacks movable parts, except for the seal, it is unlikely that when the seal 136 is pushed down, the valve 110 would fail to function.

Advantageously, the through-holes 134 are located relatively low on the spike 126. Thus, the through-holes 134 are sealed relatively early in the process as the seal 136 returns to its original configuration with the valve 110 is closed. In one preferred embodiment the through-holes 134 are located 0.075" below the spike tip 132. Additionally, the through-holes 134 are sealed even if the seal 136 does not fully return to its original configuration depicted in FIG. 2. Further, the ability of the seal 136 to return reversibly to its original position permits the reuse of the connector valve 110. Following disconnection, and before reuse, the surface of pierced seal cap 140 is essentially flush with the housing 112. Thus, this flush surface can, advantageously be sterilized with alcohol or other surface decontaminating substances. The skirt 116 and upper conduit 120 advantageously shield both connections from the surrounding environment to protect the sterility of the connection. Further, both the skirt 116 and upper conduit 120 function as collection reservoirs to prevent fluid from dripping from the valve 110 during manipulation.

A cover cap (not shown) can be supplied to fit over the upper conduit 120 as further protection for the seal surface between use. Such a cover cap, however, is not needed to maintain sterility since the seal 136 may be swabbed with a disinfectant after each use. The reversibility of the seal 136 makes the valve 110 particularly attractive as a connector valve to provide fluid communication between two fluid lines.

The valve 110 is preferably prepared from a hard plastic, but it is additionally contemplated that the valve could be prepared from other medically inert materials known to those in the art. The spike element 124 is preferably prepared from the same material as the housing 112.

In the embodiment of the invention illustrated in FIG. 2, the through-holes 134 are placed distal spike tip 132. This placement provides two important advantages. First, the placement of the through-holes 134 facilitates resealing of the valve 110 after use. Second, if the through-holes were placed at the spike tip 132, the holes 134 may core the seal cap 140 thereby introducing seal particulate into the fluid flow and possibly plugging the holes 134. Thus, the longitudinal placement of the through-holes distal spike tip 132 prevents the introduction of particulates into the fluid path and/or plugging of the through-holes 134. It is additionally contemplated that the number and diameter of the through-holes 134 can be adjusted to accommodate different fluid velocities. In a preferred embodiment, the preferred velocity of fluid passing through the through-holes 134 is equal to or greater than the flow rate through an 118 gauge needle. Through-holes larger than 118 gauge will, of course, facilitate greater fluid velocities.

An important advantage of the invention is that the valve 110 has very little dead space, thus the volume of liquid entering into the valve is substantially equivalent to the volume of fluid leaving the valve. Further, the total equivalent fluid volume of the valve is very small such that the volume of fluid flowing through the system in order to place the valve in fluid communication with a medical implement such as a syringe 146 is substantially zero.

Although this invention has been described in terms of a certain preferred embodiment, other embodiments apparent to those of ordinary skill in the art are also within the scope of this invention. Accordingly, the scope of the invention is intended to be defined only by the claims which follow. It will also be understood that the principles of the present invention disclosed herein can be applied not only to urinary catheter connectors but also to other types of catheters are other connectors used in conjunction with medical devices.

What is claimed is:

1. A urinary catheter system, comprising:
    a catheter set, comprising:
        a connector including a wall structure defining an internal cavity, said connector having a first end configured to be placed in fluid communication with a urinary catheter, said connector having a second end configured to mate with an adapter or a syringe; and
        a resealable valve located in said internal cavity movable between an open position and a closed position, said resealable valve in said closed position being configured to prevent fluid flow in a direction from said first end to said second end and in said closed position being adapted to prevent fluid flow in a direction from said second end to said first end, said resealable valve being adapted to be moved into said open position by insertion of an adapter into the second end of said connector, said resealable valve in said open position being adapted to allow fluid flow from the catheter into an adapter, said resealable valve further being adapted to be moved into said open position by insertion of a syringe into the second end of said connector, said resealable valve in said open position being adapted to allow fluid flow from a syringe into the catheter;
    a collection set adapted to be removably coupled to the catheter set, the collection set comprising:
        an adapter configured to mate with the connector of the catheter set and configured to permit fluid flow through said adapter; and
        a one-way valve proximate the adapter;
        wherein said one-way valve is configured to permit fluid flow from the catheter, through the adapter and subsequently through said one-way valve, and to impede fluid flow through said one-way valve to the adapter.

2. The urinary catheter system of claim 1, wherein said resealable valve further comprises a seal and a spike, and said seal adapted to be compressibly moved in a direction from said second end to said first end.

3. The urinary catheter system of claim 1 further comprising a syringe adapted to compressibly move said seal.

4. The urinary catheter system of claim 1 further comprising:
    a collection appliance to receive fluid from the catheter.

5. The urinary catheter system of claim 1 wherein the one-way valve is integral with the adapter.

* * * * *